United States Patent [19]

Masaki et al.

[11] 4,339,379
[45] Jul. 13, 1982

[54] N-ACRYLCARNOSINE ALUMINUM SALTS

[75] Inventors: Mitsuo Masaki, Chiba; Toru Yamanaka, Noda; Mitsuko Yoshioka, Kurihashi; Kazuki Okai, Misato, all of Japan

[73] Assignee: Nippon Chemiphar Co., Ltd., Tokyo, Japan

[21] Appl. No.: 194,844

[22] Filed: Oct. 7, 1980

[30] Foreign Application Priority Data

Dec. 26, 1979 [JP] Japan .................................. 54-168274

[51] Int. Cl.$^3$ .................. C07C 103/52; C07D 233/64; A61K 37/02; A61K 31/415
[52] U.S. Cl. ............................ 260/112.5 R; 548/104; 424/177; 424/245
[58] Field of Search ................. 260/112.5 R; 548/104, 548/101

[56] References Cited

U.S. PATENT DOCUMENTS 3,746,700  7/1973  Parisi et al. ..................... 548/101

*Primary Examiner*—Donald G. Daus
*Assistant Examiner*—Diana G. Rivers
*Attorney, Agent, or Firm*—Oblon, Fisher, Spivak, McClelland & Maier

[57] ABSTRACT

An N-acylcarnosine aluminum salt of the formula,

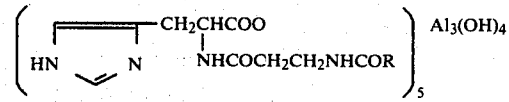

wherein R represents a lower alkyl group having 1 to 6 carbon atoms is effective for use as an anti-ulcer agent.

3 Claims, No Drawings

N-ACRYLCARNOSINE ALUMINUM SALTS

BACKGROUND OF THE INVENTION

1. Field of the Invention

This invention relates to novel N-acylcarnosine compounds, more particularly, to N-acylcarnosine aluminum salts possessing anti-ulcer effects.

2. Prior Art

In recent years, there has been a trend toward the increase of patients suffering from a digestive or peptic ulcer, and various attempts have been made to develop remedies for the ulcer.

The present inventors have synthesized a number of compounds and have investigated their pharmaceutical effects. As a result of this investigation, it has been found that N-acylcarnosine compounds of a specific type, which will appear hereinafter, exhibit a significantly excellent digestive ulcer-remedying or anti-ulcer effect and are low in toxicity and hence are satisfactory for actual use. Based upon this finding, the present invention has been accomplished.

SUMMARY OF THE INVENTION

Therefore, one object of the present invention is to provide novel N-acylcarnosine aluminum salts.

Briefly, these objects and other objects and advantages of this invention can be attained by an N-acylcarnosine aluminum salt of the formula (I),

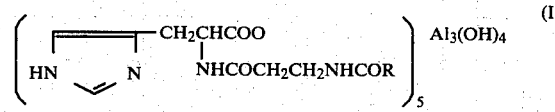

wherein R represents a lower alkyl group having 1 to 6 carbon atoms.

DETAILED DESCRIPTION OF THE PREFERRED EMBODIMENTS

The N-acylcarnosine aluminum salt of the formula (I) according to the present invention can be prepared, for example, by interacting an N-acylcarnosine of the formula (II),

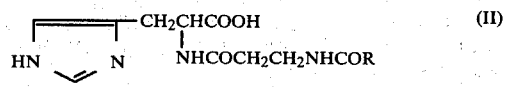

wherein R has the same meaning as defined above, with an aluminum alkoxide or an inorganic aluminum salt by any of the methods described below.

Method 1

An N-acylcarnosine is reacted with an aluminum alkoxide to obtain an N-acylcarnosine aluminum salt of the formula (I).

The N-acylcarnosine useful as one of the starting materials is prepared, for example, by converting the corresponding carboxylic acid to an acid halogenide in any usual manner and then reacting the halogenide with carnosine.

Typical examples of the aluminum alkoxide include aluminum methoxide, aluminum ethoxide, aluminum isopropoxide, aluminum t-butoxide, aluminum cyclohexyloxide and the like. When the aluminum alkoxide contains any impurity such as aluminum hydroxide or a polymer thereof, it is preferable to remove the impurity by distillation, solvent extraction or the like. The reaction is favorably conducted in a suitable solvent at a temperature ranging from room temperature to 80° C. Suitable solvents include water, an organic solvent such as methanol, ethanol, isopropanol or butanol, and a mixture thereof. After completion of the reaction, the solvent and secondarily produced alcohols are removed from the reaction solution to obtain the desired N-acylcarnosine aluminum salt of the formula (I).

Method 2

An N-acylcarnosine is reacted with an inorganic aluminum salt, and the resulting aqueous reaction solution is passed through a column packed with an anion exchange resin to obtain the desired N-acylcarnosine aluminum salt of the formula (I).

Typical examples of the inorganic aluminum salt useful in method 2 include mineral acid salts of aluminum such as aluminum sulfate, aluminum nitrate and aluminum chloride.

The anion exchange resin useful in method 2 may be either a weakly basic resin or a strongly basic resin, and preferably, a weakly basic anion exchange resin such as Amberlite IR-45 is used.

The amount of the anion exchange resin depends on the amount of the ions of a mineral acid and on the type of the ions in an aqueous solution of the N-acylcarnosine and the mineral acid. Too small amounts of such resin adversely cause the mineral acid ions to introduce into an effluent, while excessive amounts induce the adsorption of the N-acylcarnosine to an objectionable degree. Accordingly, it is desirable that the anion exchange resin be used twice or three times equivalent of the N-acylcarnosine.

The concentration of the aqueous solution which is passed through the column is not critical and is preferably held at such a level that the concentration of the mineral acid ions is in the range of about 0.5 to 1 equivalent per liter of the solution. The space velocity is suitably in the range of about 0.5 to 2.

The aqueous solution which has come out of the column is concentrated under reduced pressure and evaporated to dryness to obtain the desired compound of the formula (I).

In either method 1 or method 2 above, when the molar ratio of an N-acylcarnosine to an aluminum alkoxide or an inorganic aluminum salt is varied, an N-acylcarnosine aluminum salt can be prepared which corresponds to such molar ratio.

The N-acylcarnosine aluminum salts typical of and practical for the present invention were tested to determine their digestive ulcer-curing effects and degrees of toxicity with the results tabulated in the following experimental examples.

It will be noted that as control compounds, use was made of L-carnosine, L-glutamine, N-acetyl-L-glutamine aluminum and aluminum sucrose sulfate which are known to have an anti-ulcer effect for purposes of comparison. The anti-ulcer effects and degrees of toxicity of the N-acylcarnosine aluminum salts according to the invention were determined using rats in which instances various gastric ulcer models of rats were utilized to estimate the anti-ulcer effects.

The experimental methods of ulcers and toxicity will be apparent from the following description.

EXPERIMENT 1

Shay's ulcer: Groups of ten male Donryu strain rats each weighing 210 to 230 g were deprived of food for 48 hours. The pylorus of each rat was ligated according to the method of Shay et al [Gastroenterology, 5, 43–61 (1945)]. Each of the animals was allowed to stand abstained from food and water for further 14 hours and then sacrificed to remove its stomach. After collection of the gastric juice, the ulcerated area (mm$^2$) in the forestomach of each rat was measured under a dissecting microscope (10×). The total area (mm$^2$) of all the lesions of each rat was indicated as an ulcer index. Test medicine samples were given orally immediately after the pylorus ligation.

The experimental results are shown in Table 1.

TABLE 1
Inhibitory Effects on Shay's Ulcer in Rats

| Samples | Dose (mg/kg, P.O.) | Ulcer index | % Inhibition |
| --- | --- | --- | --- |
| Control | — | 2.9 ± 0.9 | — |
| A | 1,000 | 0.7 ± 0.8 | 75.9 |
| B | 1,000 | 0.8 ± 0.6 | 72.4 |
| N-Acetyl-L-glutamine aluminum | 2,000 | 0.9 ± 0.7 | 69.0 |
| Aluminum sucrose sulfate | 1,000 | 0.8 ± 0.6 | 72.4 |
| Control | — | 3.1 ± 1.1 | — |
| C | 1,000 | 0.8 ± 0.8 | 74.2 |
| N-Acetyl-L-glutamine aluminum | 2,000 | 1.0 ± 0.6 | 67.7 |
| Aluminum sucrose sulfate | 1,000 | 0.9 ± 0.5 | 71.0 |

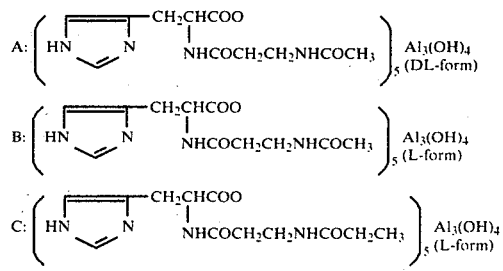

EXPERIMENT 2

Indomethacin-induced ulcer: Groups of ten male Donryu strain rats each weighing 200 to 215 g were deprived of food for 24 hours. Then, the pylorus was ligated under ether anethesia, after which indomethacin was administered subcutaneously in an amount of 25 mg/kg to each rat. Seven hours after the administration, each of the animals was sacrificed under ether anethesia to remove its stomach, followed by immersion in a 1% formalin solution for ten minutes. The stomach which had been semi-fixed was incised along its greater curvature, and the length (mm) of each lesion formed in the mucous membrane was measured under a dissecting microscope (10×). The total length (mm) of all the lesions of each rat was indicated as an ulcer index. Test medicine samples were given orally ten minutes before the pylorus legation.

The results are shown in Table 2.

TABLE 2
Inhibitory Effects on Indomethacin-induced Ulcer in Rats

| Samples | Dose (mg/kg, P.O.) | Ulcer index | % Inhibition |
| --- | --- | --- | --- |
| Control | — | 16.8 ± 2.1 | — |
| A | 300 | 6.7 ± 3.0 | 60.1 |
| B | 300 | 6.5 ± 2.5 | 61.3 |
| L-Carnosine | 300 | 17.1 ± 3.1 | ~0 |
| L-Glutamine | 300 | 9.7 ± 3.9 | 42.3 |
| Aluminum sucrose sulfate | 300 | 7.4 ± 2.8 | 56.0 |

A and B have the same meaning as defined above.

EXPERIMENT 3

Acute toxicity: Male and female Wister strain rats each weighing 150 to 200 g were divided into two groups, respectively, each group consisting of ten rats, and were administered orally with the N-acylcarnosine aluminum salts according to the invention. The thus treated rats were visually observed for seven days after the administration.

The results are shown in Table 3.

TABLE 3
Values of LD50 in Rats

| Samples | LD$_{50}$ (mg/kg, P.O.) Male | Female |
| --- | --- | --- |
| A | >10,000 | >10,000 |
| B | >10,000 | >10,000 |

A and B have the same meaning as defined above.

As is apparent from the experimental results shown in Tables 1 to 3, the N-acylcarnosine aluminum salts according to the invention exhibit an excellent inhibiting effect on various ulcer models. That is, the N-acylcarnosine aluminum salts, when administered orally in an amount of 300 to 1,000 mg/kg to rats in the tests of Shay's ulcer and indomethanocin-induced ulcer, are significantly effective for inhibiting any of the ulcers and hence are more excellent than any existing anti-ulcer agents.

In the acute toxicity test, even when the N-acylcarnosine aluminum salts were administered orally in an amount as large as 10 g/kg, no death of rats was recognized, and no or little change in general symptoms was observed.

Accordingly, the N-acylcarnosine aluminum salts of the present invention can be used as a digestive ulcer remedy which is higher in safety and more excellent in effectiveness than L-glutamine, N-acetyl-L-glutamine aluminum and aluminum sucrose sulfate which have now been widely used as anti-ulcer agents. The N-acylcarnosine aluminum salts may be administered either orally or parenterally and may be used in the form of, for example, tablets, capsules, powders, granules and syrups for oral administration and also in the form of injection for parenteral administration.

The amount of administration is generally in the range of 500 to 5,000 mg/day for adults, which may be varied depending both on the age and on the symptom.

This invention will now be described in more detail with reference to certain specific Examples which are provided for purposes of illustration only and are not intended to be considered as limiting.

EXAMPLE 1

1.39 g of aluminum isopropoxide in 20 ml of isopropyl alcohol was heated to 60° C. to which was added 3.04 g of N-acetyl-DL-carnosine at 60° C. The mixture was stirred for one hour. Thereafter, 10 ml of water was added to the reaction mixture. After stirring for 30 minutes, any insoluble materials were removed from the resulting homogeneous solution by filtration. Isopropyl alcohol of the filtrate was removed by evaporation under reduced pressure. The residual aqueous solution was freeze dried to obtain 3.35 g (quantitative yield) of an N-acetyl-DL-carnosine aluminum salt as colorless powder.

mp: 223° C. (decomp.)
NMR($D_2O$)$\delta$: 1.91 (3H, s, $COCH_3$)
2.43 (2H, t, $-COCH_2NH-$)

3.10 (2H, m, $-CH_2\overset{|}{C}HCOO$)

3.28 (2H, t, $-COCH_2CH_2NH-$)

4.44 (1H, m, $CH_2\overset{|}{C}HCOO$)

7.07, 8.25 (1H × 2, s × 2, imidazole ring protons)

These analytical data confirm the following structure (A).

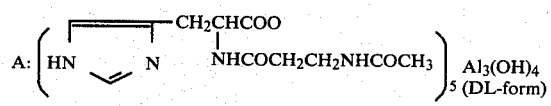

EXAMPLE 2

To a solution of 1.33 g of aluminum isopropoxide dissolved in 20 ml of isopropyl alcohol was added 2.91 g of N-acetyl-L-carnosine at 60° C., and the mixture was stirred for one hour. 10 ml of water was added to the reaction mixture which was stirred for 30 minutes until it became homogeneous. After filtration of the mixture, isopropyl alcohol of the filtrate was removed by evaporation under reduced pressure, and the residual aqueous solution was freeze dried to obtain 3.2 g (quantitative yield) of an N-acetyl-L-carnosine aluminum salt as colorless powder.

mp: 218° C. (decomp.)
$[\alpha]_D^{25}$: +19.0° C. (C = 5% in $H_2O$)
IR$\nu_{max}^{KBr}$cm$^{-1}$: 3400 (OH)
1600 (CO)
NMR($D_2O$)$\delta$: 1.91 (3H, s, $-COCH_3$)
2.43 (2H, t, $-COCH_2CH_2NH-$)

3.10 (2H, m, $-CH_2\overset{|}{C}HCOO$)

3.28 (2H, t, $-COCH_2CH_2NH-$)

4.44 (1H, m, $-CH_2\overset{|}{C}HCOO$)

7.07, 8.25 (1H × 2, s × 2, imidazole ring protons)

Elemental analysis as $(C_{11}H_{15}N_4O_4)_5Al_3(OH)_4$: Calculated (%): C 44.47, H 5.37, N 18.86. Found (%): C 44.39, H 5.34, N 18.62.

These analytical data confirm the following structure (B).

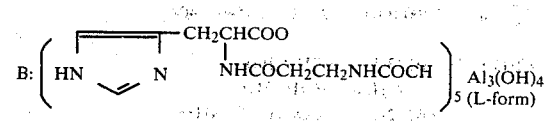

EXAMPLE 3

(a) N-Propionyl-L-carnosine:

To a solution of 2.42 of L-carnosine dissolved in 13 ml of water was added 6.5 ml of acetone. Thereafter, 4.14 g of propionyl chloride and 7.6 g of triethylamine were simultaneously added dropwise to the solution at such a rate that the reaction mixture did not exceed 20° C. in temperature and was maintained at a pH of 7.0 to 7.5. The dropwise addition took about one hour. After the addition, acetone was evaporated under reduced pressure, and the residue was adsorbed on a strong anion exchange resin (SA-10A) in an amount of 130 ml. The anion resin was washed with water and eluted with 1 N acetic acid, and the eluant was further adsorbed on a strong cation exchange resin (SK-1B) in an amount of 10 ml. After the cation resin was washed with water and eluted with 2% aqueous ammonia, the eluant was evaporated under reduced pressure to remove the greater part of ammonia. The residue was passed through 30 ml of a weak cation exchange resin (IRC-50), and the portion of the residue which had not been adsorbed was distilled to dryness under reduced pressure to obtain a crude product. Recrystallization of the crude product from methanol-acetone (2:3) gave 1.46 g of N-propionyl-L-carnosine as colorless crystal (yield: 48%).

mp: 206–209° C. (decomp.)
$[\alpha]_D^{25}$: +20.4° C. (C = 3% in $H_2O$)
IR$\nu_{max}^{KBr}$cm$^{-1}$: 3300 (OH), 1630 (CO), 1540, 1390
NMR($D_2O$)$\delta$: 1.06 (3H, t, J = 8Hz, $-CH_2CH_3$)
2.18 (2H, q, J = 8Hz, $-CH_2CH_3$)
2.44 (2H, t, J = 7Hz, $-NHCOCH_2CH_2NH-$)

3.14 (2H, m, $-CH_2\overset{|}{C}HCOO$)

3.36 (2H, t, J = 7Hz, $-NHCOCH_2CH_2NH-$)

4.44 (1H, m, $-CH_2\overset{|}{C}HCOO$)

7.08, 8.48 (1H × 2, s × 2, imidazole ring protons)

Elemental analysis as $C_{12}H_{18}N_4O_4$: Calculated (%): C 51.04, H 6.44, N 19.85. Found (%): C 50.95, H 6.43, N 19.77.

(b) To a solution of 0.76 g aluminum isopropoxide dissolved in 15 ml of isopropyl alcohol was added 1.75 g of N-propionyl-L-carnosine at 60° C. 1.9 g (quantitative yield) of an N-propionyl-L-carnosine aluminum salt was obtained as colorless powder in the same way as in Example 2.

mp: 220° C. (decomp.)

$[\alpha]_D^{25}$: +14.1° C. (C = 1% in H$_2$O)

IR$\nu_{max}^{KBr}$ cm$^{-1}$: 3400 (OH), 1640 (CO), 1540, 1400

NMR(D$_2$O)δ: 1.02 (3H, t, —CH$_2$CH$_3$)
2.10 (2H, q, —CH$_2$CH$_3$)
2.42 (2H, t, —COCH$_2$CH$_2$NH—)

3.13 (2H, m, —CH$_2$CHCOO)

3.32 (2H, t, —COCH$_2$CH$_2$NH)

4.44 (1H, m, —CH$_2$CHCOO)

7.08, 8.27 (1H × 2, s × 2, imidazole ring protons)

Elemental analysis as (C$_{12}$H$_{17}$N$_4$O$_4$)$_5$Al$_3$(OH)$_4$: Calculated (%): C 46.32, H 5.78, N 18.01. Found (%): C 46.25, H 5.72, N 17.94.

These analytical data confirm the following structure (C)

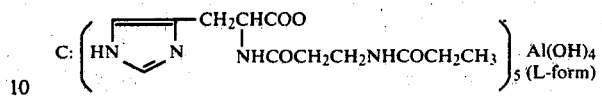

What is claimed as new and is intended to be secured by Letters Patent is:

1. An N-acylcarnosine aluminum salt of the formula (I),

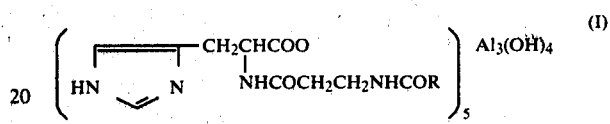

wherein R represents a lower alkyl group having 1 to 6 carbon atoms.

2. The salt of claim 1 wherein R is methyl.

3. The salt of claim 1 wherein R is ethyl.

* * * * *